United States Patent [19]

Bisping

[11] 4,233,992
[45] Nov. 18, 1980

[54] IMPLANTABLE ELECTRODE

[76] Inventor: Hans-Jürgen Bisping, Tittardshang 12, D-5100 Aachen-Laurensberg, Fed. Rep. of Germany

[21] Appl. No.: 926,097

[22] Filed: Jul. 19, 1978

[30] Foreign Application Priority Data

Jul. 19, 1977 [DE] Fed. Rep. of Germany ....... 2732547
Jul. 19, 1977 [DE] Fed. Rep. of Germany ... 225913[U]

[51] Int. Cl.³ .............................................. A61N 1/04
[52] U.S. Cl. ................................ 128/785; 128/419 P; 128/786
[58] Field of Search .................... 128/404, 418, 419 P, 128/783, 784, 785, 786

[56] References Cited

U.S. PATENT DOCUMENTS

| | | | |
|---|---|---|---|
| 3,118,439 | 1/1964 | Perrenoud | 128/2 F |
| 3,835,864 | 9/1974 | Rasor et al. | 128/418 |
| 3,868,956 | 3/1975 | Alfidi et al. | 128/345 |
| 3,939,843 | 2/1976 | Smyth | 128/419 P |
| 4,011,875 | 3/1977 | Lehr et al. | 128/418 |
| 4,057,067 | 11/1977 | Lajos | 128/418 |

FOREIGN PATENT DOCUMENTS

| | | |
|---|---|---|
| 2053919 | 5/1972 | Fed. Rep. of Germany . |
| 2133304 | 1/1973 | Fed. Rep. of Germany . |
| 2613044 | 11/1976 | Fed. Rep. of Germany . |
| 1585065 | 1/1970 | France . |
| 2187365 | 1/1974 | France . |
| 2297641 | 8/1976 | France . |
| 2302107 | 9/1976 | France . |
| 2365351 | 4/1978 | France . |
| 1316072 | 5/1973 | United Kingdom ................... 128/418 |

Primary Examiner—William E. Kamm
Attorney, Agent, or Firm—Spencer & Kaye

[57] ABSTRACT

Implantable electrode, particularly for implantation in a cardiac ventricle in order to stimulate the cardiac muscle, including an insulated electrode lead and at least one fastening element for fixing the electrode end so as to bring a conductive region forming the stimulation surface of the electrode into contact with body tissue, the fastening element being retracted in the region of the electrode end forming the electrode head so that during the insertion phase it can be accommodated substantially within the outer contour of the electrode head touched by body tissue and, in order to fix the electrode end, the fastening element is arranged to be movable relative to the outer contour of the electrode in such a manner that it comes to lie behind the frontal face of the electrode head laterally outside of the outer contour so as to engage in the body tissue.

22 Claims, 10 Drawing Figures

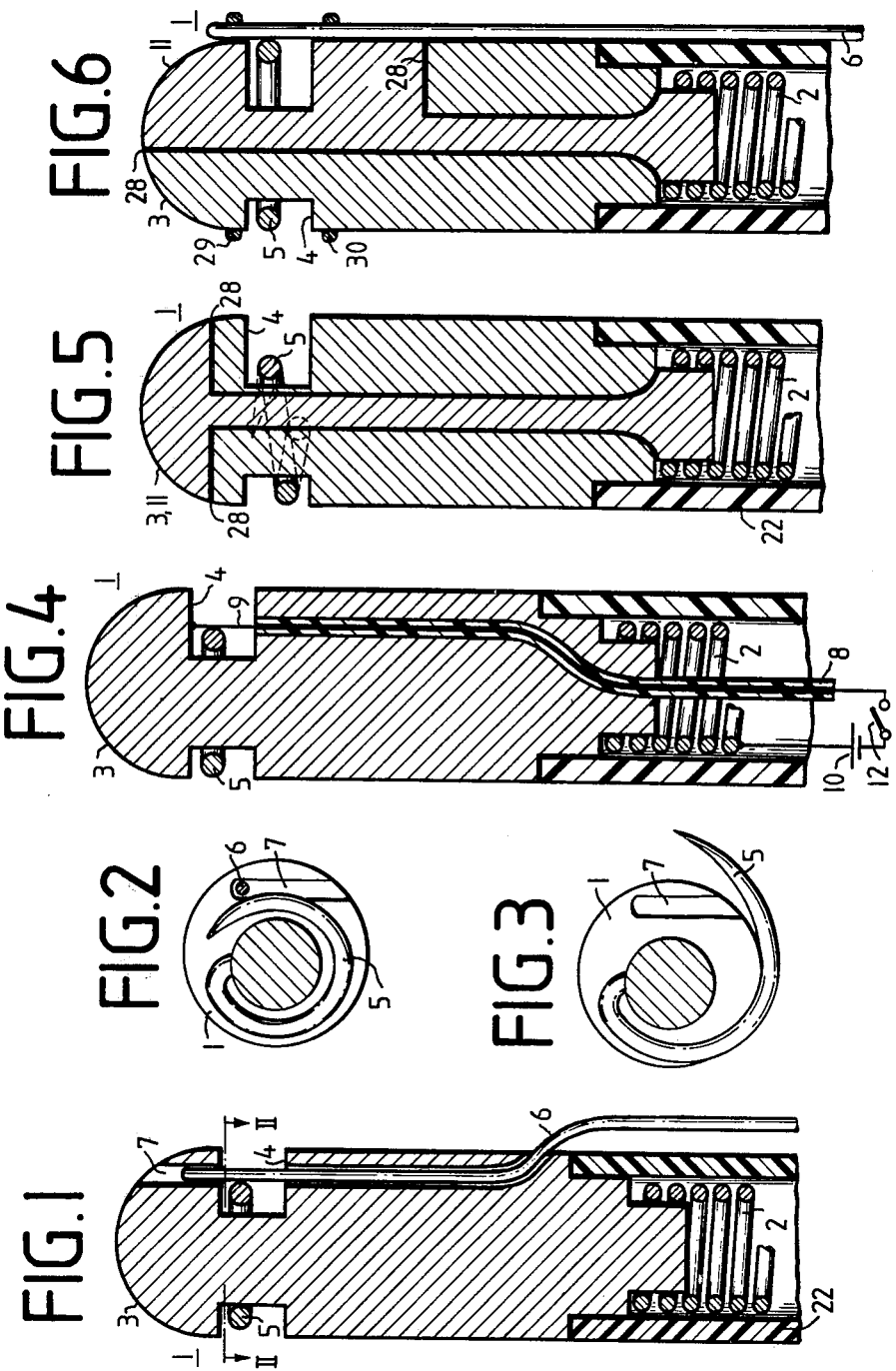

IMPLANTABLE ELECTRODE

BACKGROUND OF THE INVENTION

The present invention relates to an implantable electrode, particularly for implantation in the heart for stimulating the heart muscle, the electrode being of the type which includes an insulated electrode lead and at least one fastening element for fixing the end of the electrode so as to bring a conductive region of that end, which forms a stimulation surface, into contact with body tissue.

Implantable electrodes provide electrically conductive connections between pulse generators and tissue to be stimulated in the body of a patient. Electrodes of cardiac pacemakers serve to transmit electrical signals between the artificial cardiac pacemaker implanted in the patient's body and the end of the electrode within the heart. Since the artificial cardiac pacemaker itself must be arranged near the body's surface so as to be easily accessible by surgical procedures, but the detection of heart signals and the emission of stimulation pulses must take place directly at the heart muscle, the electrode bridges the resulting distance within the body.

In the case of endocardial implantation the electrode is advanced into the heart through a vein. Difficulties arise in these implantations due to dislocations of insufficiently fixable electrode heads as a result of cardiac movement or blood flow. In particular, if the electrode is to be fixed in the auricle, which is often desirable from a medical point of view, the smoothness of the auricle muscles creates a great tendency to dislocation.

Electrodes are known in which mechanical fixing aids in the form of metal or plastic hooks are provided to produce firm anchoring within the heart. In an electrode disclosed in German Offenlegungsschrift [Laid-open Application] No. 2,053,919, which is provided with a wire hook at its head, the selection of the point of stimulation within the heart is made difficult by the rigidity of a guide catheter provided to keep the wire hook away from body tissues during insertion of the electrode.

In other hook systems, the pressure of a guide wire disposed at the interior of the electrode is used to move out a hook mechanism that is retracted during the insertion phase, and to advance it into the cardiac tissue. During this movement, small forwardly oriented steel or nylon hooks pass out of the frontal face of the electrode head. However, they provide secure fastening of the electrode only if the electrode head is perpendicular to the tissue surface. If the electrode head comes to lie at an acute angle with respect to the tissue surface, it may happen that only one of the little hooks will come into engagement with the tissue. The structure of the known electrode is such that engagement of only one hook cannot produce a secure attachment forces, produced perhaps by the flow of blood or movements of the heart, having a certain direction may dislodge the electrode. A particular drawback is here that the bodies may perforate the tissue as tissue passes thus causing fatal situations.

It is further known, from German Offenlegungsschrift No. 26 13 044, to fasten a helically turned structure at the end of the electrode lead and to screw that structure into the cardiac tissue at the desired point by rotating the electrode lead. This known arrangement by definition results in a puncture injury in the cardiac muscle tissue so that trauma and fibrotic tissue reaction may result. Since the electrical stimulation also occurs through this helix, the inevitably resulting tissue reactions may cause an increase in the stimulation threshold of the heart. Once the stimulation threshold exceeds the amplitude of the pulses emitted by the cardiac pacemaker, the latter loses its effect.

SUMMARY OF THE INVENTION

It is therefore an object of the present invention to overcome the above drawbacks and to provide an electrode which, on the one hand, can be inserted easily and safely and is secure against dislodgement and, on the other hand, provides good electrical stimulation of the cardiac muscle with a substantially unchanging stimulation threshold.

This and other objects are accomplished according to the invention for an electrode of the above-described type by providing a fastening element which is set back, in the region of the electrode end forming the electrode head, in the axial direction of the electrode lead with respect to the frontal face of the electrode end, can be accommodated, during insertion of the electrode, substantially within the outer contour of the electrode head which contacts body tissue, and is arranged to be movable relative to the outer contour in order to fix the electrode end so that the element extends beyond the outer contour behind the frontal face of the electrode head when seen in the direction of insertion of the electrode so as to penetrate the surface of the tissue.

With this design of the electrode it is possible in an advantageous manner to effect stimulation of the body member in question essentially through the proper stimulation surface while the fastening element, pursuant to its actual function, retains the electrode head in the desired position.

The invention is based on the realization that, after insertion, the electrode head will hardly ever arrive perpendicularly to the tissue to be stimulated. Due to the trabecular network present in the heart, there will always be some tissue contacting the rear portion of the electrode head or forming a more or less acute angle with the electrode head, when the electrode head contacts the tissue surface. A fastening device which exits behind the frontal face of the electrode head utilizes this fact to achieve a secure fixing of the electrode end in this relatively stable position.

In the fixed position, the electrode end contacts the tissue surface with a slight pressure so that stimulation is possible at low potentials without the development of undesirable fibrin formation.

Preferably, the fastening element is arranged to be movable in an essentially radial direction, with respect to the axis of the electrode lead, to beyond the outer contour.

According to an advantageous embodiment of the invention, the fastening element includes at least one spiral-shaped sharp fixing hook which is provided with at least one spring winding, is fastened to the electrode head and is held in a blocking position within the outer contour by means of a blocking device. The fixing hook may be mounted in a preferably eccentrically disposed annular groove of the electrode head. Instead of a fixing hook, other elements such as, for example, clamps etc., may be used to hold the electrode head in the tissue.

According to preferred embodiments of the invention, the spiral-shaped fixing hook may be rigid, may be eccentrically rotatably mounted at the end of the electrode head or at the end of the electrode lead, respectively, and may be pivotal to outside the outer contour of the electrode head after the insertion phase is completed.

Regardless of the design of the fixing hook, it will be disposed within the outer contour of the electrode head during the insertion phase so that the electrode can be introduced through a vein and pushed therethrough to a desired location and position within the heart without injury to the veins or valves. If the desired point of stimulation has been found in the conventional manner, the blocking device for the spring-action fixing hook is released or the rigid fixing hook is pivoted out so that the hook protrudes beyond the outer contour of the electrode head. By the application of a torque to the electrode lead, preferably at the end opposite the electrode head, the sharp portion of the fixing hook comes into engagement with the heart tissue. The angle of rotation produced by this torque is limited essentially by the geometric dimensions of the fixing hook or of the annular groove, respectively.

The fixing hook may be made of a body-compatible metal with any desired cross-sectional shape and may be insulated with respect to the electrode head or the electrode lead, respectively, or may be conductively connected therewith. The fixing hook may also be made of an elastic plastic. Rotary movement in the direction opposite to that which produced engagement permits release of the fastening at any time. If the fixing hook has a screw-shaped form then, on the one hand, rotary movement produces an axial advance during engagement and, on the other hand, the hook will not be caught in any tissue or in the interior of the vein during retraction of the electrode. The danger of automatic unscrewing of the fixing hooks is reduced if the fixing hook and/or the electrode head are provided with barbs in the area of their outer contour.

The electrode according to the invention may be provided, for example, with a releasable blocking device in the form of a blocking thread, where the blocking thread is guided along the electrode lead, either inside or outside thereof, and is radially held in the area of the fixing hooks at least on one side. The blocking thread may be held radially in a groove or bore of the electrode head or by means of another thread which encircles the electrode head.

The blocking device may also be provided with a blocking hook which is mounted inside the electrode head and which can be displaced to release the fixing hook. According to a further design of the blocking device, a radially held fuse wire is provided which has at least one pole of its current source leads electrically insulated from the potential of the electrode head, i.e. the potential of the lead for transmitting the stimulation pulses. Melting of the wire releases the fixing hook. If, in dependence on the design of the electrode lead, a guide tube is employed, this may enclose the fixing hook or hooks during the insertion phase.

In designing the electrode head, it is of advantage if the stimulation surface is insulated from the remainder of the head and is disposed in the region of the frontal face of the electrode head.

According to another embodiment, the stimulation surface is extended into the region of the outer contour of the electrode head which is adjacent the portion of the fixing hook protruding beyond the outer contour. This assures that a major portion of the electrode head which comes into surface contact with tissue is taken up by the stimulation surface, which thus comes into effective electrical contact with the tissue surface.

When the electrode head is introduced into the interior of the heart through a vein, the fastening element may be released, possibly by releasing a suitable blocking device, either directly via an actuating element or indirectly and externally via an intermediarily connected further element. According to some embodiments of the invention, the latter element simultaneously advantageously seals the interior of the electrode lead against the penetration of body fluids.

BRIEF DESCRIPTION OF THE DRAWINGS

FIG. 1 is a partially schematic cross-sectional view of a first preferred embodiment of an electrode according to the invention, showing the electrode head provided with an elastic fixing hook which is held by a blocking filament or wire.

FIGS. 2 and 3 are cross-sectional views along the line II—II of FIG. 1 with the fixing hook in its blocked, or retracted, position in FIG. 2 and in its unblocked, or extended, position in FIG. 3.

FIG. 4 is a view similar to that of FIG. 1 of a similar embodiment in which the blocking device is provided in the form of a fuse wire.

FIG. 5 is a view similar to that of FIG. 1 of a further embodiment of the electrode in which the stimulation surface forms the frontal face of the electrode head and the fixing hook is fastened in an insulated manner and has a helical form.

FIG. 6 is a view similar to that of FIG. 1 of a variation of the electrode head of FIG. 5 with a lateral stimulation surface.

DESCRIPTION OF THE PREFERRED EMBODIMENTS

Figure 7:
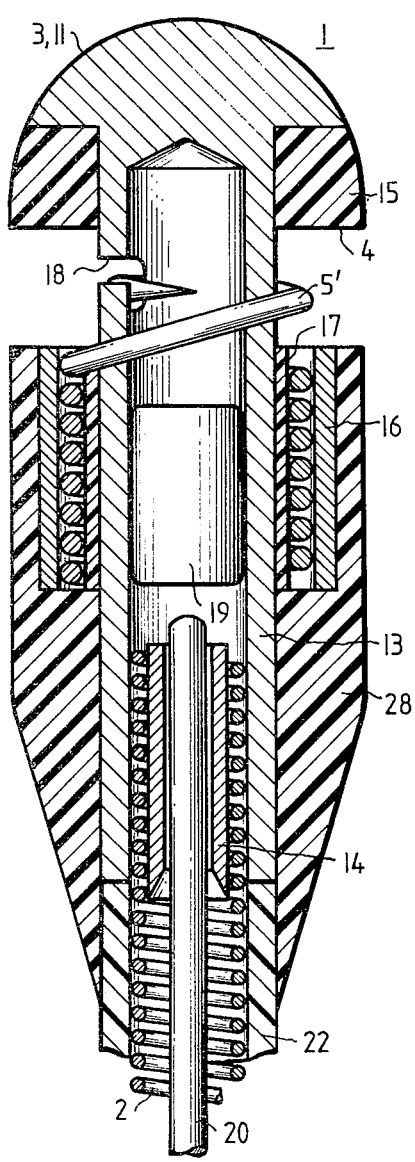
FIG. 7 is a longitudinal cross-sectional view of a further embodiment of the electrode, showing the electrode head, and in which the fixing hook is actuated by means of an additional element.

The drawing shows various embodiments and variations of the electrode according to the invention.

FIGS. 1 and 4 to 8 are schematic, longitudinal cross-sectional views of the electrode head 1 which is located near the patient's heart.

During insertion of the electrode, the electrode head is advanced through a vein, the shape of the electrode head being such that none of the fastening members protrude significantly beyond its outer contours so as to interfere with the insertion process. Once the intended position in the ventricle has been reached, a potential measurement can be effected initially, as will be described in detail below, before the fastening means are extended to hook the electrode head in place.

Extension of the fastening means in order to attach the electrode in the ventricle is actuated by the physician from the remote end of the electrode lead as soon as he has determined that the electrode head has reached a favorable position.

The design of the electrode lead including the means for connecting the electrode with the actual cardiac pacemaker corresponds to prior art designs so that a detailed description does not appear necessary. The materials employed in the embodiments to be described below are body compatible materials as they are known to those skilled in the art and described in relevant literature, and these materials can be selected according to their desired properties, e.g. electrically conductive or insulating.

FIG. 1 shows an electrode head 1 connected to a helical electrode lead 2 which is enclosed by a tubular elastic insulating member 22. A frontal face 3 of hemispherical configuration constitutes the front end of the electrode head. Behind this frontal face 3, the head 1 is provided with a peripheral annular groove 4 and the fastening element, here constituted by a fixing hook 5, is seated in groove 4 when in its retracted state. Thus the frontal face 3 of the electrode head is completely free of fastening means and may have a shape which, on the one hand, interferes as little as possible with the insertion process and, on the other hand, provides a sufficiently large contact area with the tissue surface to produce good stimulation.

The annular groove 4, which forms a recess to accommodate the fastening element, is so dimensioned that the portion of the fastening element which hooks into the tissue surface can disappear inside the outer contour of the head to such an extent that during the insertion process it will not come into engagement with the tissue contacting the electrode head even if such tissue presses against the electrode head. The recess is set back to a greater or lesser degree with respect to the frontal face 3 of the electrode head 1.

The precise geometric dimensions of the head depend on the intended location of use, but must be such that if the electrode head 1 impinges on the tissue to be stimulated during insertion and thereby extends at a more or less acute angle to the tissue surface, while supporting itself on the tissue surface, the fastening element, or at least one of them if a plurality of elements are provided, will, in the extended state, safely reach the tissue surface and come into engagement with it if the electrode is subsequently rotated about its axis. The shaft portion of head 1 which is behind the annular groove 4 and which forms the transition to the electrode lead 2 is shown relatively long in the drawing in order to increase clarity. It may be shorter than illustrated, depending on the requirements to be met.

The shape and attachment of the spiral-shaped fixing hook 5 shown in FIG. 1 and forming the fastening element is shown in FIGS. 2 and 3. It is essentially spiral-shaped and is held by a releasable blocking device formed by a blocking filament or wire 6 essentially within the contour of the electrode head. The blocking filament 6 is here loosely inserted into a slit-type groove 7 at the front of the electrode head and is supported at the bottom of that groove. The blocking filament can be easily inserted into such a groove during assembly. Behind groove 4, filament 6 passes through an internal bore in electrode head 1 or through the extension of the slit-type groove 7, and then extends outside of body 22, parallel to electrode lead 22 to a location outside of the patient's body, where it is accessible to the operating physician.

The fixing hook 5 is made of a spring material and in its relaxed, or extended, position, shown in FIG. 3, protrudes beyond the outer contour of the electrode head.

In order to save space, it is of advantage for the annular groove 4 which accommodates the fixing hook 5 to have an eccentric form, as is shown in FIGS. 2 and 3. For insertion of the electrode, the blocking filament 6 forms a barrier which the tensioned free end of the fixing hook cannot overcome, as shown in FIG. 2. Once the electrode head has reached its intended position in the heart, it is sufficient for the physician to pull the blocking filament 6 via its end which is accessible to the physician. Thus the fixing hook 5 is released and will move into the extended position shown in FIG. 3. By suitably rotating the electrode head, which can be effected by twisting the remote end of the lead 2, hook 5 will penetrate, and become secured in, the body tissue.

Instead of being inserted into a slit-type groove, the blocking filament can also be inserted into a bore or into a bore which ends in a blind bore in the front end region of electrode head 1. In this case the filament is mounted in a very stable manner and is particularly protected against accidentally slipping out.

The blocking filament 6, instead of passing outside of the electrode head, as in the embodiment shown in FIG. 1, can also extend through the interior of the electrode lead 2, in a suitably designed guide channel, and can be guided through this lead. This has the advantage that the filament cannot be inadvertently pulled back by friction forces produced during insertion and prematurely release the fixing hook.

In the embodiment shown in FIG. 4, the blocking filament is constituted by a fuse wire 9 which is surrounded by insulation 8 within the electrode head 1 and within the electrode lead 2. If, once the electrode head has reached its intended position, a voltage source, constituted by a battery 10 and a switch 12, is connected between the fuse wire 9 and the helix of lead 2, and switch 12 is closed, the resulting current will cause wire 9 to melt so that the fixing hook 5 is released. Battery 10 must be selected to provide the necessary fuse melting current.

The spiral-shaped design of the fixing hook in its outer region causes the electrode to be "tightened" in a favorable manner and thus results in an increase in contact pressure in the stimulating surface region of the electrode when the fixing hook, after having come into engagement with the tissue, penetrates deeper upon further rotation of the electrode.

In the above-illustrated embodiments, the fixing hook itself is of resilient design and has the tendency to take on a position outside of the outer contour of the electrode head. Thus the hooked position of the fastening means constitutes its stable position and this position can be reached and maintained with great certainty.

The fixing hook 5 which is made of a spring materail constitutes a structurally particularly simple embodiment. In a corresponding manner, a rigid hook may be provided which is mounted to be rotatable about a fixed axis and is brought into and retained in the pivoted-out position, for example, by means of an additional spring. A screw-like design of parts of the fixing hook can serve two different purposes, if necessary simultaneously.

In FIG. 5 the outer portion of the fixing hook 5 has a screw-like form, or pitch. This makes it possible to retract the electrode, even with the fixing hook 5 extended, if that should become necessary during an operation. If the fixing hook has a helical form in its interior portion which encloses the base of the annular groove, fastening of the hook to the electrode head can be effected in an advantageous manner, as will be described in detail below in connection with FIG. 7.

In the embodiment of FIG. 5, the stimulation surface portion 11 of frontal face 3 is insulated from the remainder of the electrode head 1 by an interposed insulating layer 28, the stimulating surface 11 coinciding essentially with the frontal face 3 of the electrode head and the stimulation region being in electrical connection with the helical lead 2. Due to the fact that the stimulation region is electrically insulated from the fastening means, in this embodiment helical hook 5, the desired defined and stable potential and resistance relationships can be established as they are required, for example, for the extended periods of operation provided for cardiac pacemakers.

In the embodiment of FIG. 6, the stimulation surface 11 extends laterally into the fastening region of the fixing hook 5. This spatial design causes the stimulating region of the electrode head to essentially coincide with that region which contacts the tissue surface. The fixing hook 5 is fastened in the portion of the electrode head (not shown in the drawing) which is electrically insulated from the stimulation surface 11 by an insulating layer 28. By electrically separating the stimulation region from the fastening means it is possible in an advantageous manner to effect a measurement of the stimulation threshold potential during implantation of the electrode without including in the result the effect of the fastening element, whose potential behavior during the course of operation of the pacemaker produces an uncertainty factor. Due to the reduced transfer resistance, the fastening element contacting the tissue would present a false, inaccurately favorable threshold potential value which, due to the above-mentioned trauma, would not be maintained during the entire period of operation of the pacemaker.

In the embodiment shown in FIG. 6, the blocking filament 6 is held against radial movement during insertion of the electrode by two bands 29 and 30 which encircle the electrode head, instead of by a groove or a bore. The bands may here also be threads or wires. Retention of the blocking filament 6 by means of encircling bands has the advantage that it simplifies manufacture.

The above-described embodiments are shown more or less schematically in the drawing. In practical devices, individual parts of the respective electrode heads themselves may be formed of a plurality of components which are held together by screws or the like.

FIG. 7 shows an electrode head which is particularly easy to manufacture. The carrier element for the electrode head 1 is a hollow cylinder 13 provided with a cap which forms the frontal face 3 and constitutes the stimulation surface 11, and which is followed by a shaped insulating body 15 preferably of silicone rubber, or of other suitable insulating material. The helical electrode lead 2 is inserted into the hollow cylinder 13 and secured to the cylinder by means of an internal metal clamping sleeve 14. The lead 2 is sheathed in insulation 22.

The hook 5' has a cylindrically, helically shaped fastening portion which is disposed around the center portion of the hollow cylinder 13 and is secured by a further metal clamping sleeve 16. In order to insulate the fixing hook 5' in its extended position, as already shown, with respect to the stimulating surface 11, an insulating tube 17, for example of polymerized tetrafluorethylene, is attached between the cylindrical helical portion of the fixing hook 5' and the hollow cylinder 13. The region of the electrode head enclosing the sleeves 14 and 16 is provided with a vulcanized insulating layer 28, also of silicone rubber or other suitable insulating material which extends from the insulation 22.

Fixing hook 5' is held in its blocking position in a manner which differs from those previously shown in that, in the retracted state, it is supported by an abutment formed adjacent a recess 18 in cylinder 13 and here takes on a stable, tensioned position. In order to release fixing hook 5', an additional element is provided which is movable in the axial direction and consists of an isolator body 19. This body is movable in the interior of hollow cylinder 13 and during insertion of the electrode remains in the position shown in FIG. 7. In its tensioned, retracted position, the fixing hook 5' extends within the outer contour of the electrode head 1 with its tip lying at the interior of the hollow cylinder 13 in such a manner that the tip will be contacted by body 19 when the latter is moved upwardly in the interior of the hollow cylinder 13. Thus the portion of fixing hook 5' which is disposed in recess 18 is lifted over the associated blocking abutment and is thus released so that it can reach its extended position in which it extends laterally beyond head 1 and can hook into adjacent body tissue.

A guide wire 20 extends through lead 2 and serves mainly to reinforce, or rigidify, the electrode during insertion through a vein. At the end of insertion, body 19 is advanced by the end of guide wire 20, body 19 being disposed in force transitting relation between the guide wire 20 and the fixing hook 5'. Thus it is only necessary, in order to fix the electrode in place, for the physician to push the guide wire 20 forward until body 19 pushes on the tip of fixing hook 5 and thus releases the hook from recess 18. To facilitate insertion of the guide wire 20 into the clamping sleeve 14, the opening of sleeve 14 which faces electrode lead 2 is widened in the shape of a funnel.

If the body 19 is made of a material which is opaque to X-rays, it is possible to additionally check during implantation by means of X-rays whether the body has reached its position in the electrode head which assures release of the fixing hook 5' since the electrode head also can be discerned with sufficient clarity on a radiogram.

In this embodiment it is of particular advantage that no additional transmission element is required to actuate the fixing hook 5' from the remote end of the electrode. In the illustrated mode of blocking the hook, which employs an abutment, it is also possible to initially test release the fixing hook outside of the body and then to return it to its retracted, tensioned position for implantation pushing back body 19 with auxiliary means through a bore not shown in FIG. 7.

The body 19, which may be made of insulating material as well as of metal, simultaneously serves the important purpose of sealing the interior of the electrode lead from the body fluids which could enter through the opening formed by recess 18 and which could otherwise result in annoying hardening of the electrode leads. The use of such a sealingly acting intermediate element is, as can be seen, of particular advantage whenever the actuation of the fastening element is to be effected from the interior of the electrode head through an opening which leads to the outside.

Figure 8:
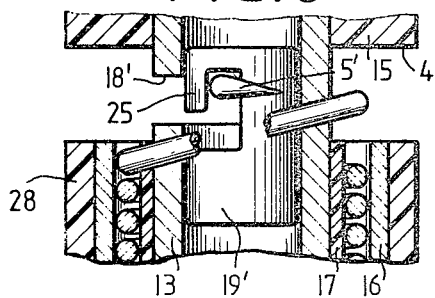
FIG. 8 is a detail view of a modified form of construction of the embodiment of FIG. 7.

The intermediate element may also be a barrier type member, such as the body 19' shown in FIG. 8 in a variation of the embodiment of FIG. 7. Body 19' presents a hook member 25 which retains the fixing hook 5' in its retracted, tensioned position in coaction with a suitable configuration of the recess 18' until it is released by an appropriate movement of body 19', which in the case of the structure shown in FIG. 8 is an upward movement.

Figure 9:
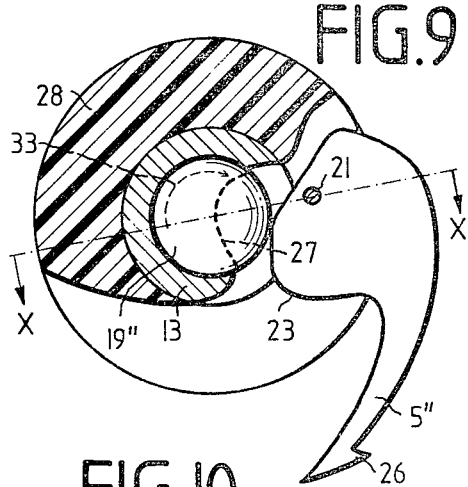
FIG. 9 is an axial, cross-sectional view of a modified form of construction of the fixing hook of the embodiment of FIG. 7.
Figure 10:
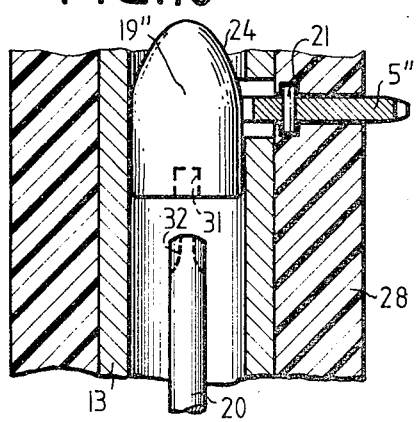
FIG. 10 is a longitudinal cross-sectional view of a part of the electrode head along the line X—X of FIG. 9.

FIGS. 9 and 10 show, for a variation of the electrode head of FIG. 7, how the fixing hook may be designed if no spring forces are to be used. A fixing hook 5" is here essentially rigid and is mounted to be rotatable about an axis 21.

Hook 5" is disposed in a recess formed in insulating layer 28 and hollow cylinder 13, which recess has the irregular form shown by a solid line in FIG. 9. A protrusion 23 forming part of hook 5" is disposed within the hollow cross section of the hollow cylinder 13 and takes up the broken line position 27 when the hook 5" is in the folded-in, or retracted, position. If a body 19" which is axially movable within hollow cylinder 13, has a conical taper 24 shown in FIG. 10, it will press the protrusion 23 of hook 5" out of the interior region of hollow cylinder 13, and thus push the fixing hook 5" into its folded-out, or extended, position, when it is pushed upwardly. The line of contact of protrusion 23 of fixing hook 5" with the region of the taper 24 of body 19" forms a type of cam control which determines the movement of hook 5" in dependence on the axial advance of body 19".

The friction between body 19" and the interior wall of hollow cylinder 13 is here of such magnitude that body 19" cannot undergo any independent movement. If it has been pushed, for example, into its final position within the cylinder by guide wire 20, it has such dimensions that its outer peripheral face prevents folding back of hook 5" so that the latter is held stably in its extended position.

The fixing hook 5" employed in this embodiment additionally is provided with a barb 26 at its end which additionally retains it in its hooked position in body tissue and further secures the fixing of the electrode.

Folding out of the fixing hook 5" by displacement of its protrusion 23 from the open cross section of the hollow cylinder under the action of the outer face of body 19" in the manner of a control cam can also be effected by rotation of body 19". For this purpose, the body 19" is provided with a recessed slot 31 (shown in dashed lines in FIG. 10) at its end facing the electrode lead and the guide wire 20 has a corresponding screwdriver extension 32 (also shown in dashed lines) for engagement in this slot. If the body 19" is now additionally rotatably mounted at the level of the fixing hook 5" and if its cross section has a recess which, for example, follows the dashed outline 27 of FIG. 9, the fixing hook 5" can be folded in, in order to insert the electrode head, with body 19" in the corresponding position, so that its protrusion 23 comes to lie in the recess following outline 27 (not shown). If the body 19" is now turned after insertion of the electrode by means of the guide wire 20 which has been provided with the screwdriver extension 32, in the direction of the dashed arrow 33 (FIG. 9) the surface of the body 19" in the region of outline 27 presses the protrusion 23 out of the interior region of the hollow cylinder 13 and the hook 5" is folded out.

It can be seen that with the electrode according to the invention different favorable possibilities exist for different requirements in the release of the fastening means. Thus, for example, the body 19" shown in FIG. 10 could also have its original position in the end of the front portion of the electrode head 1 and be connected with a wire or filament which passes through the interior of the head 1 and out of the electrode lead 2. If body 19" is tapered at its other end, the fixing hook 5" could then also be pivoted out by pulling on this filament.

It will be understood that the above description of the present invention is susceptible to various modifications, changes and adaptations, and the same are intended to be comprehended within the meaning and range of equivalents of the appended claims.

What is claimed is:

1. In a body implantable electrode including an electrode head having a stimulation surface at its end, an insulated electrode lead and at least one fastening element for fixing the electrode so as to bring the stimulation surface into contact with body tissue, the improvement wherein: said fastening element is disposed at a location spaced behind said end of said electrode head in the axial direction of said electrode lead; said fastening element is arranged to be in a retracted position, during insertion of said electrode, substantially within the outer contour of said electrode head which is touched by body tissue during insertion, and said fastening element is arranged to be moved essentially in the radial direction, normal to the axial direction of said electrode lead, beyond the outer contour of said electrode head, into an extended position in which it extends laterally beyond such outer contour at a location behind said end of said electrode head, with respect to the direction of insertion of said electrode, so as to penetrate in the body tissue surface and fix said electrode in place; said electrode further comprises fastening element control means guided within said electrode lead and controllable from the end of said electrode lead remote from said electrode head for effecting movement of said fastening element from its retracted position to its extended position, and an intermediate element separate from, and acted on by, said control means for effecting such movement of said fastening element; said electrode head comprises a hollow cylinder connected to said electrode lead; and said intermediate element extends along the inside of said cylinder and movingly and sealingly engages the interior wall of said cylinder to act as a seal against the intrusion of body fluids.

2. An arrangement as defined in claim 1 wherein said fastening element comprises at least one fixing hook and said electrode head is provided with a recess into which said hook can be retracted.

3. An arrangement as defined in claim 2 wherein said fixing hook extends essentially tangentially to the lateral outer contour of said electrode head.

4. An arrangement as defined in claim 2 wherein said fixing hook has, at least in part, a spiral shape.

5. An arrangement as defined in claim 2 wherein said fixing hook is essentially rigid and is pivotally mounted for movement beyond the outer contour of said electrode head.

6. An arrangement as defined in claim 1 wherein said intermediate element comprises releasable blocking means for holding said fastening element in its retracted position.

7. An arrangement as defined in claim 1 wherein said hollow cylinder is provided with a lateral opening at which said intermediate element can enter into interaction with said fastening element.

8. An arrangement as defined in claim 1 wherein said intermediate element is shaped such that said fastening element is moved, by operation of said control means, to its extended position laterally beyond the outer contour of said electrode head.

9. An arrangement as defined in claim 8 wherein said intermediate element has a surface formed to contact said fastening element in the manner of a control cam for controlling the movement of said fastening element.

10. An arrangement as defined in claim 1 wherein said fastening element comprises at least one fixing hook presenting a free end which extends laterally beyond such outer contour when said fastening element is away from its retracted position, and said intermediate element presents a blocking hook arranged to engage said fixing hook near its free end to hold said fastening element in its retracted position.

11. An arrangement as defined in claim 1 wherein said intermediate element is of a material which is opaque to X-rays.

12. An arrangement as defined in claim 1 wherein said fastening element comprises at least one fixing hook arranged to be movable essentially in the radial direction relative to said electrode head, with the free end of said fixing hook being subjected to a spring force which is directed essentially radially outwardly.

13. An arrangement as defined in claim 12 wherein the end of said fixing hook remote from its free end faces the interior of said electrode head and is essentially clamped firmly therein, and said fixing hook is made of a spring material.

14. An arrangement as defined in claim 1 wherein said intermediate element comprise releasable blocking means for holding said fastening element in its retracted position, said blocking means and said fastening element being movable relative to one another for releasing said fastening element for movement into its extended position.

15. An arrangement as defined in claim 14 wherein said intermediate element is arranged to be pushed from the region of the end of said electrode lead remote from said electrode head for releasing said fastening element for movement into its extended position.

16. An arrangement as defined in claim 15 wherein said control means serve to reinforce said electrode during insertion.

17. An arrangement as defined in claim 14 wherein said blocking means define an opening delimiting an abutment arranged to hold said fastening element in its retracted position.

18. An arrangement as defined in claim 1 wherein said fastening element has at least one barb.

19. An arrangement as defined in claim 1 wherein said fastening element is electrically insulated from said stimulation surface.

20. An arrangement as defined in claim 1 wherein said stimulation surface is disposed essentially in the region of the end of said electrode head.

21. An arrangement as defined in claim 1 wherein said stimulation surface is disposed essentially in the region of said fastening element.

22. An arrangement as defined in claim 1 wherein said electrode is to be implanted in the heart of a patient for stimulation of the cardiac muscle.

* * * * *